United States Patent
Jouve et al.

(10) Patent No.: US 6,753,441 B1
(45) Date of Patent: Jun. 22, 2004

(54) METHOD FOR PREPARING P-HYDROXYMANDELIC COMPOUNDS OPTIONALLY SUBSTITUTED

(75) Inventors: Isabelle Jouve, Genas (FR); Frederic Fournet, Couzon au Mont d'Or (FR); Jean Fragnon, Meyzieu (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/719,839
(22) PCT Filed: Jun. 16, 1999
(86) PCT No.: PCT/FR99/01442
§ 371 (c)(1),
(2), (4) Date: Mar. 14, 2001
(87) PCT Pub. No.: WO99/65853
PCT Pub. Date: Dec. 23, 1999

(30) Foreign Application Priority Data

Jun. 16, 1998 (FR) .......................................... 98 07586

(51) Int. Cl.⁷ .............................................. C07C 69/76
(52) U.S. Cl. ...................................................... 560/60
(58) Field of Search ............................ 560/60; 562/470

(56) References Cited

U.S. PATENT DOCUMENTS

| | | | | |
|---|---|---|---|---|
| 4,165,341 A | * | 8/1979 | Umemura et al. .......... 260/600 |
| 4,337,355 A | | 6/1982 | Nakajima et al. ........... 562/478 |
| 4,339,602 A | * | 7/1982 | Schouteeten et al. ....... 562/466 |
| 4,401,830 A | | 8/1983 | Umumura et al. .......... 562/478 |
| 5,248,816 A | | 9/1993 | Shuttleworth et al. ...... 562/470 |

FOREIGN PATENT DOCUMENTS

| EP | 0 578 550 | | 1/1994 | ......... C07C/51/367 |
|---|---|---|---|---|
| WO | WO 94/14746 | * | 7/1994 | ........... C07C/56/52 |

OTHER PUBLICATIONS

Chem Abstract 57:57394; Pisano, J et al Clin. Chim Acta (1962), 7, 285–291.*
Chem Abst 66:102382 Wybenzo D. et al Clinica Chimica Acta (1967) 16(1) 147–54.*
D.I. Sychev, "Carboxylic Acids of Different Structure as Bifuntional Catalysts", Chemical Abstracts, 117:191094 (Zh. Org. Khim., vol. 28 (1992), pp. 149–153).*

* cited by examiner

Primary Examiner—Paul J. Killos
(74) Attorney, Agent, or Firm—Burns, Doane, Swecker & Mathis, L.L.P.

(57) ABSTRACT

The invention concerns a method for preparing p-hydroxymandelic compounds optionally substituted and their derivatives. More particularly, it concerns a method for preparing p-hydroxymandelic acid and methoxy-3 p-hydroxymandelic acid and their derivatives. The invention concerns a method for preparing p-hydroxymandelic compounds optionally substituted and their derivatives, which consists in condensing in water, in the presence of an alkaline agent, an aromatic compound bearing at least a hydroxyl group and whereof the position in para is free, with glyoxylic acid, said method being characterised in that the reaction is carried out in the presence of an efficient amount of a compound bearing at least two carboxylic functions.

30 Claims, No Drawings

METHOD FOR PREPARING P-HYDROXYMANDELIC COMPOUNDS OPTIONALLY SUBSTITUTED

A subject of the present invention is a process for the preparation of optionally substituted p-hydroxymandelic compounds and derivatives.

In the disclosure of the invention which follows, the term, "optionally substituted p-hydroxymandelic compounds" is used to refer to an aromatic compound which carries at least one —CHOH—COOH group in para position of a hydroxyl group.

The present invention relates, more particularly, to the preparation of p-hydroxymandelic acid and 3-methoxy p-hydroxymandelic acid.

One of the conventional synthesis routes for p-hydroxymandelic acids consists in carrying out the condensation, in alkaline medium, of glyoxylic acid on phenol and/or its corresponding derivatives.

The yield is limited by the fact that the condensation reaction is not selective and also produces o-hydroxymandelic acids and dimandelic acids.

Furthermore, the reaction yield is reduced due to a parasitic secondary reaction. In fact, glyoxylic acid in aqueous alkaline medium is converted according to Caniizaro's reaction into oxalic and glycolic acids.

In order to prevent this Cannizaro's reaction from becoming dominant and destroying the glyoxylic acid, a proposal has been made in FR-A 2 132 364 for the condensation reaction to be carried out in a dilute aqueous medium and at low temperature or ambient temperature.

In view of the difficulty in obtaining satisfactory reaction yields, it is important to control the various parameters of the process, and, in particular, the quality of the glyoxylic acid used.

The most worthwhile process from an industrial viewpoint for the preparation of glyoxylic acid consists in oxidising the glyoxal with nitric acid. In this way, aqueous solutions of glyoxylic acid are obtained, which, in addition to unreacted glyoxal, also contain oxalic acid, organic acids, such as formic acid, acetic acid, glycolic acid, and nitric acid.

Until now, new methods have been constantly sought for the separation and purification of glyoxylic acid.

Therefore, a process was proposed in DE-A 1 198 339 which first and foremostly permitted the nitric acid to be eliminated, followed by the oxalic acid using basic ion exchange resins, followed by the glyoxal and the other impurities by over-concentration of the solution and crystallisation.

In DE-A 2 501 743, a process was disclosed in which the glyoxylic acid is separated from these impurities by extraction using aliphatic or cycloaliphatic alcohols, or aliphatic esters of alcohols with low carbon condensation.

A process for obtaining aqueous solutions of glyoxylic acid free from other acids has also been described in FR-A 2 552 426 which consists in treating the starting solution with an organic nitrogenous compound, preferably a tertiary amine, at a temperature which is at the most equal to 50° C., then in extracting the glyoxylic acid by extraction of the organic phase with water, at a higher temperature.

A constant concern has therefore been noted in the prior art of providing a solution of glyoxylic acid which is free of impurities.

Running counter to this teaching, it has been found that within the scope of preparing optionally substituted p-hydroxymandelic compounds condensation of glyoxylic acid and of the corresponding phenol is carried out with an increased yield, provided that said reaction is carried out in the presence of a dicarboxylic acid used in a certain quantity.

A precise subject of the present invention is a process for the preparation of optionally substituted p-hydroxymandelic compounds and derivatives, which consists in carrying out the condensation, in water, in the presence of an alkaline agent, of an aromatic compound with at least one hydroxyl group and the para position of which is free, with glyoxylic acid, said process being characterised in that the reaction is carried out in the presence of an effective quantity of a catalyst compound with at least two carboxylic functions.

In accordance with the process of the invention, the use of a catalyst according to the invention allows the reaction yield to be increased.

Another advantage of the process according to the invention is that it can involve a more technical glyoxylic acid containing, inter alia, oxalic acid.

The process according to the invention is used, most particularly, with phenol but also with substituted phenols which have at least one non-substituted para position.

The aromatic nucleus has at least one hydroxyl group, but it can also have one or more other substituents. Generally, "several substituents" means less than four substituents per aromatic nucleus.

Any substituent can be present provided that it is does not interfere in the reaction of the invention.

Therefore, the process according to the invention is well suited for use with hydroxylated aromatic compounds corresponding to the following formula (I):

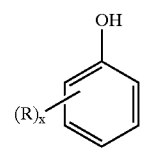

(I)

in which formula (I):
  the para position is free,
  x is an integer between 1 and 4,
  R represents:
    a hydrogen atom,
    a hydrocarbon group having from 1 to 20 carbon atoms selected from the alkyl, alkoxy, hydroxyalkyl, cycloalkyl, aryl, phenoxy, alkoxyalkyl, fluoroalkyl, hydroxyalkoxyalkylene groups,
    a hydroxyl group,
    a —CHO group,
    an acyl group having from 2 to 6 carbon atoms,
    a halogen atom, preferably a fluorine, chlorine or bromine atom,
    two R groups placed on two vicinal carbon atoms can form together with the carbon atoms to which they are attached, a benzene ring.
  Examples of R radicals which can be attached to the aromatic nucleus are given hereinafter:
    alkyl radicals, such as methyl, ethyl, propyl, isopropyl, butyl, isobutyl, sec-butyl, tert-butyl, n-octyl, 2-ethyl hexyl, decyl, octadecyl, eicosly,
    alkoxy radicals, such as methoxy, ethoxy, propoxy, isopropoxy, butoxy, isobutoxy, sec-butoxy, tert-butoxy, hexyloxy, decyloxy, hexadecylocy, octadecylocy, or a phenoxy radical,
    hydroxyalkyl radicals, such as hydroxymethyl, hydroxyethyl, hydroxypropyl, hydroxyhexyl, hydroxydecyl, cycloalkyl radicals, such as cylcopentyl, cyclohexyl, cycloheptyl, fluoroalkyl radicals, such as fluoromethyl, difluoromethyl, trifluoromethyl, fluoroethyl, 1,1,1-trifluoro ethyl, pentafluoroethyl, fluoropropyl, fluorobutyl, tribluoroamyl, hydroxyalkyoxyalkylene radicals, such as hydroxymethyloxyethylene, hydroxyethyl di-(oxyethylene), hydroxyethyl tri-(oxyethylene), 1,2-hydroxyethyloxypropylene, hydroxyethyloxybutylene, hydroxypropyloxypropylene, hydroxybutyloxybutylene, hydroxybutyl di-(oxybutylene), halogen atoms, such as fluorine, chlorine, bromine, or iodine.

Quite preferably, hydroxylated aromatic compounds are used in the process of the invention, corresponding to the general formula (I), in which:

x is equal to 0, 1,2 or 3,

R represents one of the following groups or functions:
a hydrogen atom,
a linear or branched alkyl radical having from 1 to 10 carbon atoms, and preferably from 1 to 4 carbon atoms,
a linear or branched alkoxy radical having from 1 to 10 carbon atoms, preferably from 1 to 4 carbon atoms,
an —OH group,
a —CHO group,
a halogen atom,
a —CF$_3$ group.

Still more preferably, the compounds of formula (I) are selected in which the R radicals which are identical or different are a hydrogen atom, a linear or branched alkyl radical with 1 to 4 carbon atoms, such as the methyl, ethyl, n-propyl, isopropyl, n-butyl or isobutyl radicals, a linear or branched alkoxy radical having 1 to 4 carbon atoms, such as the methoxy or ethoxy radicals, a —CHO group, or a chlorine atom, and x is preferably equal to 0 or 1.

By way of illustration of compounds corresponding to formula (I), the following can be mentioned:
  those corresponding to formula (I) in which x is equal to 0, such as phenol,
  those corresponding to formula (I) in which x is equal to 1, such as
    pyrocatechin
    resorcin
    o-cresol
    m-cresol
    2-ethyl phenol
    3-ethyl phenol
    2-propyl phenol
    2-sec-butyl phenol
    2-tert-butyl phenol
    3-tert-butyl phenol
    2-methoxy phenol (guaiacol)
    3-methoxy-phenol
    2-ethoxy phenol (guetol)
    2-isopropoxy phenol
    salicylic aldehyde
    methyl salicylate
    2-chloro phenol
    3-chloro phenol
    3-nitro phenol
  those corresponding to formula (I) in which x is equal to 2, such as:
    2,3-dimethyl phenol
    2,5-dimethyl phenol
    3,5-dimethyl phenol
    2-hydroxy 5-acetamido benzaldehyde
    2-hydroxy 5-ethamido benzaldehyde
    2,3-dichloro phenol
    2,5-dichloro phenol
    3.5-dichloro phenol
    pyrogallol
  those corresponding to formula (I) in which x is equal to 3, such as:
    2,3,5-trimethyl phenol
    3,5-di-tert butyl phenol
    2,3,5-trichloro phenol
  those corresponding to formula (I) having a naphthalenic radical, such as:
    1-naphthol
    2-naphthol
    1,2-dihydroxy naphthalene
    1,5-dihydroxy naphthalene
    2,3-dihydroxy naphthalene
    2,6-dihydroxy naphthalene
    2,7-dihydroxy naphthalene
    6-bromo 2-naphthol
  those corresponding to formula (I) having a chain formation of benzene nuclei:
    2-phenoxy phenol
    3-phenoxy phenol Of the list of afore-mentioned compounds, the aromatic compounds preferably used which have at least one hydroxyl group are: phenol, o-cresol, m-cresol, 3-ethyl phenol, 2-tert-butyl phenol, guaiacol, guetol.

As regards the type of catalyst used, an at least difunctional acid can be used which corresponds to the following formula (II):

$$HOOC-R_1-COOH \qquad (II)$$

in which formula (II), $R_1$ represents a valency bond or an optionally substituted hydrocarbon radical containing 1 to 40 carbon atoms.

To be more exact, in formula (II), $R_1$ symbolises a substituted or non-substituted hydrocarbon radical which can be a linear or branched, saturated or unsaturated acyclic aliphatic radical; a monocyclic or polycyclic, saturated, unsaturated, or aromatic carbocyclic radical; a monocyclic or polycyclic, saturated, unsaturated or aromatic heterocyclic radical.

The compounds with at least two carboxylic functions of general formula (II) in which $R_1$ represents a valency bond or a divalent radical preferably having 1 to 15 carbon atoms are quite particularly suitable for implementation of the process according to the invention.

The compounds with at least two carboxylic functions of general formula (II) in which $R_1$ represents a linear or branched, saturated or unsaturated aliphatic residue are particularly well suited for use of the process according to the invention.

To be more exact, $R_1$ represents a linear or branched, acyclic aliphatic residue having preferably 1 to 12 carbon atoms, saturated or containing one or more unsaturations on the chain, generally 1 to 3 unsaturatiors which can be single or conjugated double bonds, or triple bonds.

The hydrocarbon chain can optionally be:
(1)—interrupted by one of the following groups called Y:

—O—;  —CO—;  —COO—;  —N—;
                                    |
                                    $R_2$

—CO—N;  —S—;  —SO$_2$—
     |
     $R_2$ in which formula $R_2$ represents hydrogen or a linear or branched alkyl radical having 1 to 4 carbon atoms, preferably a methyl or ethyl radical, or a radical of —(CH$_2$)$_p$—COOH type in which p is a number between 1 and 5,
(2)—and/or bearing one of the following substituents:
—OH; —COOH; —CHO; —NO$_2$; —CN; —NH$_2$; —SH; —X; CF$_3$
—NH—[(CH$_2$)$_p$—COOH] or —N—[(CH$_2$)$_p$—COOH]$_2$
with X representing a halogen atom, preferably a fluorine, chlorine or bromine atom, and p having the meaning given hereinabove.

The compounds with at least two carboxylic functions of general formula (II) in which $R_1$ represents a monocylic or polycyclic hydrocarbon residue are also suitable for implementation of the process according to the invention.

$R_1$ preferably represents an aromatic hydrocarbon residue, and, in particular, a benzene residue corresponding to the general formula (III):

(III)

($R_3$)$_n$ in which formula (III):
n is an integer from 0 to 4, preferably from 0 to 3,
$R_3$ represents ones of the following groups or functions,
    a hydrogen atom,
    a linear or branched alkyl radical having from 1 to 4 carbon atoms,
    a linear or branched alkoxy radical having from 1 to 4 carbon atoms,
    a methylene or ethylene dioxy radical,
    a —CHO group,
    a phenyl or benzyl radical,
    a halogen atom,
Even more preferably, the compounds of formula (II) are selected in which the $R_1$ radical corresponds to formula (III) in which the $R_3$ radicals, which are identical or different, are a hydrogen atom, a methyl radical, a methoxy radical, a —CHO group.

The compounds having at least two carboxylic functions can correspond to general formula (II) in which the $R_1$ radical represents a polycyclic aromatic hydrocarbon divalent residue; the rings can form between themselves ortho condensed, ortho- and peri-condensed systems. More particularly, a naphthylenic residue can be mentioned; said rings being able to be substituted by 1 to 4 $R_3$ radicals, preferably by 1 to 3, $R_3$ having the meanings stated hereinabove for the substituents of the aromatic hydrocarbon residue of general formula (III).

In general formula (II) of the compounds with at least two carboxylic functions, $R_1$ can also represent a carbocyclic residue which is saturated or which comprises 1 or 2 unsaturations in the ring, generally having from 3 to 7 carbon atoms, preferably 6 carbon atoms in the ring; said ring being able to be substituted by 1 to 5, preferably 1 to 3, $R_3$ radicals, $R_3$ having the meanings stated hereinabove for the substituents of the aromatic hydrocarbon residue of general formula (III).

As preferred examples of $R_1$ radicals the cyclohexanediyl radicals can be mentioned which are optionally substituted by linear or branched alkyl radicals having 1 to 4 carbon atoms.

The compounds with at least two carboxylic functions can also correspond to formula (II) in which $R_1$ represents a divalent radical constituted by a chain formation of two to four residues as defined hereinabove, an aliphatic residue, an aromatic residue, or a cycloaliphatic residue. These can be connected together by a valency bond or by a function group which can be, in particular, a group selected from the groups called Y.

Some examples of $R_1$ radicals are given hereinafter:
—CH$_2$—C$_6$H$_4$—;
—CH$_2$—CH$_2$—C$_6$H$_4$—;
—CH$_2$—O—C$_6$H$_4$—;
—CH$_2$—O—C$_6$H$_4$—;
—CH$_2$—O—C$_6$H$_4$—CH$_2$—;
—C$_6$H$_4$—C$_6$H$_4$—;
—C$_6$H$_4$—CH$_2$C$_6$H$_4$—;
—C$_6$H$_4$—O—C$_6$H$_4$—;
—CH$_2$—C$_6$H$_4$—CH$_2$—C$_6$H$_4$—CH$_2$—

The following compounds with at least two carboxylic functions can be mentioned, quite particularly, by way of catalysts which are suitable for the present invention:
dicarboxylic aliphatic acids, such as:
    oxalic acid
    malonic acid
    succinic acid
    glutaric acid
    adipic acid
    2,4-dimethyl adipic acid
    pimelic acid
    suberic acid
    azelaic acid
    sebacic acid
    dodecane dioic acid
    fumaric acid
    maleic acid
cycloalkanedicarboxylic acids, such as cyclohexane 1,4-dicarboxylic acid,
aromatic dicarboxylic acids, such as:
    phthalic acid
    isophthalic acid
    terephthalic acid
    phenylenediacetic acid
    naphthalene 1,5-dicarboxylic acid
    naphthalene 1,6-dicarboxylic acid
    4,4'-diphenylcarboxylic acid
    3,3'-diphenylcarboxylic acid
    bis(4-hydroxycarbonyl)phenyl oxide
    bis(3-hydroxycarbonyl)phenyl oxide
    4,4'-dihydroxycarbonyl diphenylsulphone
    3,3'-dihydroxycarbonyl diphenylsulphone
pyrimidine or imidazole dicarboxylic acids.

In the afore-mentioned list of dicarboxylic acids, the compounds preferably used are: oxalic acid, malonic acid, succinic acid, glutaric acid, adipic acid, sebacic acid, phthalic acid, isophthalic acid, terephthalic acid.

Aminopolycarboxylic acids are also perfectly well suited for implementation of the process according to the invention. As examples of aminopolycarboxylic acids suitable for use in the process of the invention mention can be made of the following, inter alia:

ethylenediaminotetracetic acid (E.D.T.A.)
diethylenetriaminopentacetic acid (D.T.P.A.)
nitrilotriacetic acid (N.T.A.)
N-(2-hydroxyethylethylene diaminotriacetic acid (H.E.D.T.A.)

Of the afore-mentioned aminopolycarboxylic acids, ethylenediaminotetracetic acid is preferably selected.

According to the process of the invention, the reaction is carried out in the presence of an alkali metal hydroxide which can be sodium or potassium hydroxide.

For economic considerations, sodium hydroxide is preferably selected.

With regard to the concentrations and quantities of reagents to be used, the preferred conditions are defined hereinbelow.

In accordance with the process according to the invention a solution of glyoxylic acid is used. The concentration of said solution is not critical and can vary greatly, e.g. between 15 and 70% by weight. Preferably, commercial solutions are used, the concentration of which is approximately 50%.

According to the process of the invention, the glyoxylic acid is reacted on the excess of the hydroxylated aromatic compound of formula (I). The molar ratio between the hydroxylated aromatic compound of formula (I) and the glyoxylic acid varies between 1.5 and 4.0 and is preferably selected between 2.0 and 3.0.

The alkali metal hydroxide solution used has a concentration which is generally between 10 and 50% by weight. The concentration of the starting solution is not critical. However, as the concentration of the hydroxylated aromatic compound of formula (I) is advantageously low in the reaction medium, a dilute solution of alkali metal is used to carry out the dilution of the reaction medium.

The quantity of alkali metal hydroxide introduced into the reaction medium takes account of the quantity necessary to salify the hydroxyl function of the hydroxylated aromatic compound of formula (I) and of the quantity necessary to salify the carboxylic function of the glyoxylic acid.

If the hydroxylated aromatic compound of formula (I) has salifiable functions other than the hydroxyl group, the quantity of alkali metal hydroxide necessary to salify all the salifiable functions which can be hydroxyl groups and/or COOH carboxylic functions is therefore introduced.

Generally, the quantity of alkali metal hydroxide can vary greatly and be equal to, or approximately equal to, the stoichiometry, or in excess. Generally, the quantity of alkali metal hydroxide varies between 80 and 120% of the stoichiometric quantity.

The concentration of the hydroxylated aromatic compound of formula (I) is preferably between 0.5 and 1.5 moles/liter, and, more particularly, in the region of 1 mole/liter. With regard to the quantity of catalyst used, this is determined in such a way that the molar ratio between the catalyst and the hydroxylated aromatic compound of formula (I) is between 0.005 and 0.025, and preferably between 0.01 and 0.02.

The quantity of catalyst used, as expressed by the ratio between the number of moles of catalyst and the number of moles of glyoxylic acid is advantageously selected to be between 0.5 and 2.5%, preferably between 1 and 2%.

The preferred catalyst is oxalic acid.

The commercial solutions of glyoxalic acid can contain very low quantities of oxalic acid. The oxalic acid of the reaction can therefore be provided, in part, by the starting solution. In this case, it will be necessary to complete the quantity of oxalic acid by the addition of oxalic acid or of any other dicarboxylic acid in order that the afore-mentioned ratios are observed.

According to a preferred embodiment of the invention, a solution of glyoxylic acid is advantageously used containing between 0.6 and 3%, preferably between 1.2 and 2.6%, by weight of oxalic acid, expressed in relation to the weight of glyoxylic acid.

The reaction temperature is advantageously selected between 20° C. and 60° C., and preferably between 30° C. and 40° C.

The process according to the invention is carried out at atmospheric pressure, but under a controlled inert gas atmosphere, preferably nitrogen or rare gases, in particular nitrogen.

A preferred practical embodiment of the invention will be given hereinafter.

The solution of glyoxylic acid and catalyst, and, in parallel, the solution of alkali metal hydroxide employed in a quantity necessary to salify the COOH function are introduced into a reaction medium containing the hydroxylated aromatic compound of formula (I), water and the alkali metal hydroxide in a quantity necessary to salify the hydroxyl group and other possible salifiable functions of the compound of formula (I).

The reaction mediun is kept under agitation and at the temperature selected within the aforementioned range for a variable period ranging from 1 to 10 hours.

Another variant of the execution of the invention consists in adding the reaction catalyst not to the aqueous solution of glyoxylic acid but simultaneously with the hydroxylated aromatic compound of formula (I).

At the end of the reaction, the optionally substituted p-hydroxymandelic acid obtained is separated in salified form using conventional separation techniques, in particular crystallisation.

The process according to the invention is quite particularly well suited when an aqueous solution of glyoxylic acid is used containing monofunctional acids, such as formic and glycolic acid, and, in particular, when acetic acid is present in a concentration which is variable between 0.1 and 3%.

The process according to the invention results in the production of optionally substituted p-hydroxymandelic compounds which can be represented by the following formula (I):

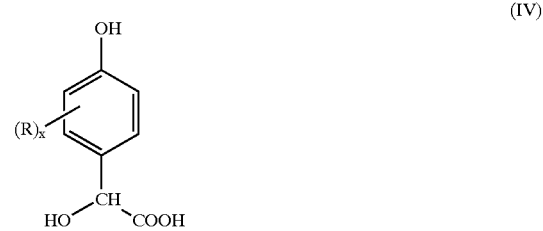

(IV)

in which formula (IV) R and x have the meaning given in formula (I).

These products are particularly worthwhile since they are intermediate products, which, inter alia, allow hydroxyarylacetic acids to be obtained by reduction and hydroxyarylglyoxylic (=hydroxyaryl α-oxo acetic) acids or hydroxyaromatic aldehydes to be obtained by oxidation.

A preferred use of the invention is the preparation of hydroxyaromatic aldehydes by oxidation of the compounds of formula (IV) obtained according to the invention.

The oxidation of the compounds of formula (IV) can be carried out according to the techniques described in writings. Thus, reference can be made to P. HEBERT [Bull. Soc. Chim. France, 27, p. 45–55 (1920)] and to NAGAI SHIGEKI et al [JP-A 76/128934]. The oxidation is generally carried out using oxygen or air under pressure, in the presence of an appropriate catalyst, such as derivatives of chromium, cobalt, copper, vanadium or osmium, for example.

Therefore, the invention allows easy access to 4-hydroxy benzaldehyde and to vanillin and its analogues, e.g. 3-ethyl, 3-isopropyl vanillin, by oxidation respectively of p-hydroxymandelic acid and of 3-methoxy p-hydroxymandelic acids, and 3-ethoxy p-hydroxymandelic or 3-isopropoxy p-hydroxymandelic acids.

The following examples illustrate the invention, without however limiting it.

In the examples, the percentages stated are expressed by weight.

The abbreviations mentioned in the examples have the following meanings:

| | | |
|---|---|---|
| Conversion (TT) | = | number of moles of guaiacol converted / number of moles of guaiacol introduced |
| Yield (RR) | = | number of moles of mandelic acid formed / number of moles of guaiacol introduced |
| Selectivity (RT) | = | number of moles of mandelic acid formed / number of moles of guaiacol converted |

EXAMPLE 1

600 g distilled water, 91.6 g (0.687 mol) of a 30% aqueous soda solution, 93 g (0.750 mol) guaiacol are introduced into a 1-liter glass reaction vessel equipped with a double jacket, a pH electrode, a temperature probe, a condenser, an inert gas supply, and a mechanical agitation device.

An inert atmosphere is established, and the reaction mixture is brought to 35° C., and 50.7 g (0.380 mol) of a 30% by weight aqueous soda solution and 55.2 g of a 50% by weight aqueous glyoxylic acid solution are added simultaneously over a period of 2 hours. Oxalic acid is added with the glyoxylic acid introduced in such a quantity that it represents 0.75% by weight of the glyoxylic acid solution.

The glyoxylic acid solution introduced contains 0.3% oxalic acid, 0.9% lower carboxylic acids such as acetic acid, and formic acid and glycolic acid in a respective quantity of less than 0.1%.

The reaction mixture is maintained at 35° C. for 2 hours.

At the end of the reaction, the reaction products are analysed using high performance liquid chromatography.

The results obtained were as follows:

conversion:
    TT=47.3%

4-hydroxy 3-methoxy mandelic acid:
    RR=79.7%
    RT=84.2%

2-hydroxy 3-methoxy mandelic acid:
    RR=4.8%
    RT=5.1%

2-hydroxy 3-methoxy 1,5-dimandelic acid:
    RR=8.0%
    RT=4.0%

COMPARATIVE EXAMPLE 2

Example 1 is reproduced, except that no oxalic acid is introduced.

The results obtained were as follows:

conversion:
    TT=46.1%

4-hydroxy 3-methoxy mandelic acid:
    RR=76.9%
    RT=83.0%

2-hydroxy 3-methoxymandelic acid:
    RR=5.1%
    RT=5.5%

2-hydroxy 3-methoxy 1,5-dimandelic acid:
    RR=7.5%
    RT=4.1%

EXAMPLE 3

In this example, Example 1 is reproduced except that a 50% solution of glyoxylic acid is used containing 0.4% by weight of oxalic acid.

The results obtained are as follows:

conversion:
    TT=48%

4-hydroxy 3-methoxy mandelic acid:
    RR=79.3%
    RT=83.1%

2-hydroxy 3-methoxy mandelic acid:
    RR=5.6%
    RT=5.8%

2-hydroxy 3-methoxy 1,5-dimandelic acid:
    RR=8.0%
    RT=4.2%

EXAMPLES 4 to 8

In the following set of examples Example 1 is reproduced except that different types of dicarboxylic acids are used, such as malonic acid, succinic acid and E.D.T.A.

The glyoxylic acid solution used contains oxalic acid at a rate of 0.09%, lower carboxylic acids such as acetic acid at a rate of 1%, formic acid and glycolic acid at respective quantities of less than 0.3%.

All the conditions of the examples and the results obtained are indicated in Table I.

TABLE I

| Ref. ex. | Dicarboxylic acid (%) | TT | RR para | RR ortho | RR di | RT para | RT ortho | RT di |
|---|---|---|---|---|---|---|---|---|
| 4 | — | 45.2 | 77.5 | 4.9 | 7.6 | 84.3 | 5.3 | 4.1 |
| 5 | oxalic acid (2.0%) | 47.8 | 80.1 | 4.8 | 8.1 | 83.0 | 5.0 | 4.2 |
| 6 | malonic acid (2.0%) | 46.1 | 80.2 | 5.2 | 7.6 | 84.8 | 5.5 | 4.1 |
| 7 | succinic acid (1.9%) | 48.0 | 81.4 | 5.6 | 8.0 | 85.0 | 5.8 | 4.2 |
| 8 | E.D.T.A. (1.5%) | 44.5 | 80.6 | 4.9 | 7.7 | 88.0 | 5.4 | 4.2 |

*= dicarboxylic acid expressed in molar percent in relation to the glyoxylic acid.

EXAMPLES 9 to 11

In the following examples, the quantity of oxalic acid used in the glyoxylic acid solution is increased.

The procedure of Example 1 is followed, and a 50% glyoxylic acid solution is used, the composition of which is given in Examples 4 to 8.

The results obtained are indicated in the following table:

TABLE II

| Ref. ex. | Oxalic acid* | TT | RR | | | RT | | |
|---|---|---|---|---|---|---|---|---|
| | | | para | ortho | di | para | ortho | di |
| 9 | 1.00 | 45.2 | 79.5 | 5.1 | 7.6 | 86.7 | 5.6 | 4.1 |
| 10 | 1.9 | 47.8 | 80.1 | 4.8 | 8.1 | 83.0 | 5.0 | 4.2 |
| 11 | 1.78 | 46.1 | 76.5 | 4.8 | 8.0 | 83.0 | 5.2 | 4.3 |

*= concentration of oxalic acid in % by weight in the glyoxylic acid solution.

In said table, the abbreviations, "ortho", "para" and "di" mean:

4-hydroxy 3-methoxy mandelic acid=para
2-hydroxy 3-methoxy dimandelic acid=ortho
2-hydroxy 3-methoxy 1,5 dimnandelic acid=di

What is claimed is:

1. A process for the preparation of an optionally substituted p-hydroxymandelic compound, comprising condensing, in water and in the presence of an alkaline agent, (1) a hydroxylated aromatic compound with (2) glyoxylic acid, the para-position of said hydroxylated aromatic compound being free and said condensation being carried out in the presence of a catalytically effective amount of (3) a polycarboxylic compound.

2. A process according to claim 1, wherein the hydroxylated corresponds to the following formula (I):

$$\underset{(R)_x}{\text{OH}} \text{—benzene ring} \qquad (I)$$

in which formula (I):
the para position is free,
x is an integer 1 and 4,
R represents:
  a hydrogen atom,
  a hydrocarbon group having from 1 to 20 carbon atoms selected from the alkyl, alkoxy, hydroxyalkyl, cycloalkyl, aryl, phenoxy, alkoxyalkyl, fluoroalkyl, hydroxyalkoxyalkylene groups,
  a hydroxyl group,
  a CHO group,
  an acyl group having from 2 to 6 carbon atoms,
  a halogen atom,
  two R groups placed on two vicinal carbon atoms can form together and with the carbon atoms which carry them a benzene ring.

3. A process according to claim 1, wherein the hydroxylated aromatic compound corresponds to formula (I), in which:
x is equal to 0, 1, 2 or 3,
R represents one of the following groups or functions:
  a hydrogen atom,
  a linear or branched alkyl radical having from 1 to 10 carbon atoms,
  a linear or branched alkoxy radical having from 1 to 10 carbon atoms,
  an —OH group,
  a —CHO group,
  a halogen atom,
  a —CF$_3$ group.

4. A process according to claim 1, wherein the hydroxylated aromatic compound corresponds to formula (I) in which the R radicals which are identical or different are a hydrogen atom, a linear or branched alkyl radical with 1 to 4 carbon atoms, a linear or branched alkoxy radical with 1 to 4 carbon atoms, a —CHO group, a chlorine atom, and x is equal to 0 or 1.

5. A process according to claim 1, wherein the hydroxylated aromatic compound of formula (I) is selected from the group consisting of phenol, o-cresol, m-cresol, 3-ethyl phenol, 2-tert-butyl phenol, guaiacol, guetol, and 2-isopropoxy phenol.

6. A process according to claim 1, wherein the quantity of alkali metal hydroxide is the stoichiometric quantity necessary to salify all the salifiable groups of the hydroxylated aromatic compound of formula (I) and to salify the carboxylic function of the glyoxylic acid.

7. A process according to claim 6, wherein the catalyst is a compound carrying at least two carboxylic functions corresponding to the following formula (II):

$$\text{HOOC—R}_1\text{—COOH} \qquad (II)$$

in which formula (II), $R_1$ represents a valency bond or an optionally substituted hydrocarbon radical containing 1 to 40 carbon atoms.

8. A process according to claim 7, wherein the catalyst is a compound having at least two carboxylic functions corresponding to formula (II) wherein $R_1$ symbolises a substituted or non-substituted hydrocarbon radical which can be a linear or branched, saturated or unsaturated acyclic aliphatic radical; a monocyclic or polycyclic, saturated, unsaturated, or aromatic carbocyclic radical; a monocyclic or polycyclic, saturated, unsaturated or aromatic heterocyclic radical.

9. A process according to claim 7, wherein the catalyst is a compound with at least two carboxylic functions corresponding to formula (II), in which $R_1$ represents a linear or branched, acyclic aliphatic residue having 1 to 12 carbon atoms, saturated or containing one or more unsaturations on the chain which can be single or conjugated double bonds, or triple bonds-, the hydrocarbon chain can optionally be:

(1)—interrupted by one of the following groups called Y:

$$\text{—O—;} \quad \text{—CO—;} \quad \text{—COO—;} \quad \underset{R_2}{\text{—N—}};$$

$$\underset{R_2}{\text{—CO—N;}} \quad \text{—S—;} \quad \text{—SO}_2\text{—}$$

in which formulae $R_2$ represents hydrogen or a linear or branched alkyl radical having 1 to 4 carbon atoms, or a radical of —(CH$_2$)$_p$—COOH type in which p is a number between t and 5, (2)—and/or bearing one of the following substituents:
  —OH; —COOH; —CHO; —NO$_p$; —CN; —NH$_2$; —SH; —X; CF$_3$
  —NH—[(CH$_2$)$_p$—COOH] or —N—[(CH$_2$)$_p$—COOH]$_2$
  with X representing a halogen atom, and p having the meaning given hereinabove.

10. A process according to claim 7, wherein the catalyst is a compound with at least two carboxylic functions corresponding to formula (II), in which $R_1$ represents a benzene residue corresponding to the general formula (III):

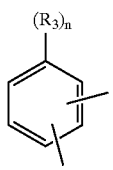

(III)

in which formula (III):
 n is an integer from 0 to 4,
 $R_3$ represents one of the following groups or functions,
  hydrogen atom,
  linear or branched alkyl radical having from 1 to 4 carbon atoms,
  linear or branched alkoxy radical having from 1 to 4 carbon atoms,
  methylene or ethylene dioxy radical,
  —CHO group,
  phenyl or benzyl radical,
  halogen atom.

11. A process according to claim 7, wherein the catalyst is a compound with at least two carboxylic functions corresponding to formula (II) in which the R1 radical represents a polycyclic aromatic hydrocarbon divalent residue; the rings can form between themselves ortho-condensed, ortho- and peri-condensed systems.

12. A process according to claim 7, wherein the catalyst is a compound with at least two carboxylic functions corresponding to formula (II), in which $R_1$ represents a carbocyclic residue which is saturated or contains 1 or 2 unsaturations in the ring.

13. A process according to claim 7, wherein the catalyst is a compound with at least two carboxylic functions corresponding to formula (II), in which $R_1$ represents a divalent radical constituted by a chain formation of two to four residues as defined hereinabove, an aliphatic residue, an aromatic residue or a cycloaliphatic residue, connected together by a valency bond or by a function group.

14. A process according to claim 7, wherein the catalyst is a compound with at least two carboxylic functions corresponding to formula (II) selected from the group consisting of:
 oxalic acid
 malonic acid
 succinic acid
 glutaric acid
 adipic acid
 2,4-dimethyl adipic acid
 pimelic acid
 suberic acid
 azelaic acid
 sebacic acid
 dodecane dioic acid
 fumaric acid
 maleic acid
 cyclohexane 1,4-dicarboxylic acid,
 phthalic acid
 isophthalic acid
 terephthalic acid
 phenylenediacetic acid
 naphihalene 1,5-dicarboxylic acid
 naphtlalene 1,6-dicarboxylic acid
 4,4'-diphenylcarboxylic acid
 3,3'-diphenylcarboxylic acid
 bis(4-hydroxycarbonyl)phenyl oxide
 bis(3-hydroxycarbonyl)phenyl oxide
 4,4'-dihydroxycarbonyl diphenylsulphone
 3,3'-dihydroxycarbonyl diphenylsulphone
 ethylenediaminotetracetic acid (E.D.T.A.)
 diethylenetriaminopentacetic acid (D.T.P.A.)
 nitrilotriacetic acid (N.T.A.) and
 N-(2-hydroxyethyl)ethylene diaminotriacetic acid (H.E.D.T.A.).

15. A process according to claim 1, wherein the aqueous solution of glyoxylic acid contains monofunctional acids.

16. A process according to claim 1, wherein the aqueous solution of glyoxylic acid has a concentration which varies from 15 to 70% by weight.

17. A process according to claim 1, wherein the molar ratio between the hydroxylated aromatic compound of formula (I) and the glyoxylic acid varies between 1.5 and 4.0.

18. A process according to claim 1, wherein the concentration of the hydroxylated aromatic compound of formula (I) is between 0.5 and 1.5 moles/liter.

19. A process according to claim 1, wherein the quantity of catalyst used is such that the molar ratio between the catalyst and the hydroxylated aromatic compound of formula (I) is between 0.005 and 0.025, and preferably between 0.01 and 0.02.

20. A process according to claim 1, wherein the quantity of catalyst used, as expressed by the ratio between the number of moles of catalyst and the number of moles of glyoxylic acid, is selected between 0.5 and 2.5%.

21. A process according to claim 1, wherein the catalyst is entirely or partly provided by the aqueous solution of glyoxylic acid.

22. A process according to claim 21, wherein the solution of glyoxylic acid comprises between 0.6 and 3%, by weight, of oxalic acid, as expressed in relation to the weight of glyoxylic acid.

23. A process according to claim 1, wherein the catalyst is introduced with the aqueous solution of glyoxylic acid or into the starting reaction medium containing the hydroxylated aromatic compound of formula (I), water and the alkali metal hydroxide.

24. A process according to claim 1, wherein the temperature of the reaction varies between 20° C. and 60° C.

25. A process for the production of 4-hydroxy benzaldehydes by oxidation of an optionally substituted p-hydroxymandelic acid obtained in accordance with the process of claim 1.

26. A process for producing hydroxyarylacetic acids comprising reducing the optionally substituted p-hydroxymandelic compounds obtained according to the process of claim 1.

27. A process for producing hydroxyarylglyoxylic acids or hydroxyaromatic aldehydes which comprises oxidizing the optionally substituted p-hydroxymandelic compounds obtained according to the process of claim 1.

28. The process according to claim 25, wherein 3-methoxy-p-hydroxymandelic acid is oxidized to vanillin.

29. The process according to claim 25, wherein 3-ethoxy-p-hydroxymandelic acid is oxidized to ethylvanillin.

30. The process according to claim 25, wherein 3-isopropoxy-p-hydroxy mandelic acid is oxidized to isopropylvanillin.

* * * * *